US012472294B2

(12) United States Patent
Jansson et al.

(10) Patent No.: US 12,472,294 B2
(45) Date of Patent: Nov. 18, 2025

(54) PERITONEAL DIALYSIS SYSTEM AND METHOD FOR MINIMIZING PATIENT DRAIN PAIN

(71) Applicants: BAXTER INTERNATIONAL INC., Deerfield, IL (US); BAXTER HEALTHCARE SA, Glattpark (CH)

(72) Inventors: Olof Jansson, Vellinge (SE); Michael Pettersson, Malmo (SE)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 432 days.

(21) Appl. No.: 18/125,374

(22) Filed: Mar. 23, 2023

(65) Prior Publication Data

US 2023/0330313 A1 Oct. 19, 2023

Related U.S. Application Data

(60) Provisional application No. 63/323,617, filed on Mar. 25, 2022.

(51) Int. Cl.
*A61M 1/28* (2006.01)
*A61M 1/14* (2006.01)

(52) U.S. Cl.
CPC ............ *A61M 1/28* (2013.01); *A61M 1/1565* (2022.05); *A61M 1/159* (2022.05); *A61M 1/284* (2014.02); *A61M 1/155* (2022.05); *A61M 2205/3331* (2013.01); *A61M 2205/3334* (2013.01); *A61M 2205/3344* (2013.01)

(58) Field of Classification Search
CPC .... A61M 1/155; A61M 1/1565; A61M 1/159; A61M 1/28; A61M 1/284; A61M 2205/3331; A61M 2205/3334; A61M 2205/3344
See application file for complete search history.

(56) References Cited

U.S. PATENT DOCUMENTS

2014/0088493 A1 * 3/2014 Pan ........................ A61M 1/281
73/37.5

FOREIGN PATENT DOCUMENTS

WO WO 2021/102012 A1 * 5/2021

* cited by examiner

*Primary Examiner* — John Kim
(74) *Attorney, Agent, or Firm* — K&L Gates LLP

(57) ABSTRACT

A peritoneal dialysis ("PD") system includes a PD fluid pump; a patient line for receiving used PD fluid pumped by the PD fluid pump during a patient drain; a pressure sensor positioned and arranged to sense a negative pressure associated with the PD fluid pumped during the patient drain; and a control unit configured to (i) determine or know a flowrate of the PD fluid pumped during the patient drain, (ii) determine an applied negative pressure at which the PD fluid pump is to pump the PD fluid during the patient drain, the applied pressure based on a pressure drop corresponding to the determined or known flowrate, and (iii) use sensed negative pressure from the pressure sensor to cause the PD fluid pump to pump the PD fluid during the patient drain at the applied negative pressure.

20 Claims, 5 Drawing Sheets

PERITONEAL DIALYSIS SYSTEM AND METHOD FOR MINIMIZING PATIENT DRAIN PAIN

RELATED APPLICATIONS

This application claims priority to U.S. Provisional Patent App. No. 63/323,617, entitled "PERITONEAL DIALYSIS SYSTEM AND METHOD FOR MINIMIZING PATIENT DRAIN PAIN," filed Mar. 25, 2022, the entire contents of which are incorporated herein by reference herein and relied upon.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, to drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

APD patients may experience what is known as drain pain. The negative pressure applied to the patient's peritoneal cavity during drain may cause pain, especially for new patients where the peritoneal cavity may be extra sensitive. The pain level may be to the level that the patient no longer wishes to continue an APD treatment. Certain APD machines are configured to supply negative pumping pressure using pneumatic or air pressure applied to an air side of one or more flexible membrane or diaphragm. The negative pressure sucks the flexible membrane or diaphragm inwardly, causing used PD fluid or effluent to be pulled from the patient along a fluid side of the flexible membrane or diaphragm. The negative pneumatic pressure applied is constant, which means that the applied pressure is the same regardless of the conditions present at the patient, which are not constant.

The conditions present at the patient change. For example, the patients' sleeping position changes assuming a nighttime treatment in which the patient is sleeping. Also, the volume of effluent residing within the patient's peritoneal cavity changes over the course of a patient drain. Each of these changing conditions affects the flowrate of used PD fluid or effluent flowing along the patient line back to the APD machine. The flowrate affects the amount of pressure drop along the patient line, where the higher the flowrate the higher the pressure drop.

In low flow patient conditions, e.g., where the patient's sleeping position has somehow limited drain flowrate, or the patient's peritoneal cavity is almost empty, creating a lack of effluent supply situation, the corresponding pressure drop will be low. A constant negative pressure applied for both high and low drain flowrates will create an environment for patient drain pain during low drain flowrates.

A need exists accordingly for an improved APD system that mitigates or eliminates patient drain pain.

SUMMARY

The present disclosure sets forth an automated peritoneal dialysis ("APD") system that mitigates or eliminates drain pain. The APD system includes an APD machine or cycler. The APD machine is capable of delivering fresh, heated PD fluid to the patient at, for example, 14 kPa (2.0 psig) or higher. The APD machine is capable of removing used PD fluid or effluent from the patient at, for example, −9 kPa (−1.3 psig) or an even greater negative pressure. The resulting flowrate to or from the patient may be dependent on a number of factors, including where the patient is located elevationally compared to the APD machine's pumping portion, the patient's sleeping position (assuming a nighttime treatment), and for a patient drain, the amount of effluent remaining in the patient's peritoneal cavity.

The pressure in the patient's peritoneal cavity is typically low, only somewhat above the atmospheric pressure, for example, a typical patient full of two liters of PD fluid has an average peritoneal cavity pressure of about 12 cmH2O (≈8.8 mmHg, 1.18 kPa, 0.17 psig) according to C Brandes, et al., "Optimization of Dialysate Flow and Mass Transfer During Automated Peritoneal Dialysis", AJKD volume 25, No 4, April, 1995. When used PD fluid or effluent is plentiful in the peritoneal cavity at the start of a patient drain cycle, a flow of 100 to 350 ml/min may be reached by the APD machine of the present disclosure. The flowrate is dependent on the relative elevational distance between the APD machine's pumping portion and the patient's peritoneal cavity. The relatively high flowrate creates a relatively high pressure drop in the patient line tube, so that a negative pressure of, e.g., −9 kPa (−1.3 psig) applied at the APD machine will be significantly lower (less negative) at the distal or patient end of the patient line, e.g., around −1 kPa (−0.15 psig).

A problem may arise at the end of a patient drain for example. Effluent is in less supply and the peritoneal membrane may start to enclose around the catheter, causing the pressure drop between the inside of the patient's indwelling catheter and the peritoneal cavity to increase, decreasing drain flow. The lowered drain flowrate causes the pressure drop in the patient line to decrease. If the applied negative pressure were to remain at the high flowrate setting, e.g., −9 kPa (−1.3 psig), the negative pressure that the patient sees increases, which may lead to drain pain. In fact, if the drain flowrate falls to zero, the patient would see the full negative drain pressure, which may even be increased by a head height delta between the APD machine and the patient's peritoneal cavity. The APD system of the present disclosure does not let this happen.

The APD system of the present disclosure employs an APD machine with the ability to adjust at least an applied negative pressure (and possibly an applied positive pressure) and to measure at least a patient drain flowrate (and possibly a patient fill flowrate). During a patient drain, a control unit for the APD machine periodically checks the current flowrate (or periodically looks to update a flowrate commanded by control unit 60). The control unit uses the current flowrate to determine a corresponding pressure drop along the patient line. The corresponding pressure drop may be determined in a plurality of ways. Described herein are equations for determining the corresponding pressure drop based on certain knowns relating to the configuration and material used for the patient line, the viscosity and density of the PD fluid used (e.g., dependent on composition, e.g., glucose content), PD fluid temperature, and the measured PD fluid flowrate. The corresponding pressure drop may be determined alternatively using one or more lookup table that correlates pressure drop to measured flowrate. The lookup table may be populated using the equations discussed herein.

Knowing the pressure drop for the current flowrate, the control unit causes the negative patient drain pumping pressure to be adjusted so that the resulting effluent pressure at the patient's peritoneal cavity is at a level that will likely not cause drain pain, e.g., at or around the standing still, patient full pressure of 12 cmH2O (≈8.8 mmHg, 1.18 kPa, 0.17 psig). By periodically checking the current patient drain flowrate (or periodically looking to update a patient drain flowrate commanded by control unit 60) and updating the applied negative patient drain pressure, the control unit of the present system maintains the natural (patient full) patient pressure over the course of each patient drain of a PD treatment. The overall effect is to reduce, and perhaps greatly reduce, the likelihood of patient drain pain.

The system and associated methodology of the present disclosure are also advantageous because they allow drain time to be reduced by pulling at a higher flowrate when effluent is plentiful in the patient's peritoneal cavity. In systems not modeling pressure drop according to the present disclosure, the negative pressure applied may be limited to the safe negative pressure limit at the patient, e.g., −9 kPa (−1.3 psig or perhaps more negative due to head height), even in times of high flowrate, which is selected so as not to damage the patient's peritoneum. By modeling the pressure drop along the patient line, the PD machine of the present disclosure may apply a higher negative pressure during times of high flowrate, e.g., −14 kPa (−2.0 psig), knowing that due to the determined pressure drop, the pressure at the patient will fall to a safe level. Applying the higher pressure during times of high flowrate speeds the patient drain and reduces the time needed for the drain. It has been reported that patient fills and drains account for 35% to 55% of the total treatment time, see Alp Akonour, et al., "A Mathematical Model to Optimize the Drain Phase in Gravity-Based Peritoneal Dialysis Systems", Advances in Peritoneal Dialysis, Vol. 26, 2010. Reducing patient drain time accordingly leaves more time for patient dwells in which treatment takes place and/or shortens the overall treatment.

The system and associated methodology may also be advantageous because it may allow the cost of the patient line and associated disposable set to be lowered due to the patient line being made of a less expensive material. The reason for the less expansive material is because the pressure drop optimization of the present disclosure minimizes the risk of collapsing the patient line while applying negative pressure to the patient.

In light of the disclosure set forth herein, and without limiting the disclosure in any way, in a first aspect of the present disclosure, which may be combined with any other aspect, or portion thereof, a peritoneal dialysis ("PD") system includes a PD fluid pump; a patient line for receiving used PD fluid pumped by the PD fluid pump during a patient drain; a pressure sensor positioned and arranged to sense a negative pressure associated with the PD fluid pumped during the patient drain; and a control unit configured to (i) determine or know a flowrate of the PD fluid pumped during the patient drain, (ii) determine an applied negative pressure at which the PD fluid pump is to pump the PD fluid during the patient drain, the applied pressure based on a pressure drop corresponding to the determined or known flowrate, and (iii) use sensed negative pressure from the pressure sensor to cause the PD fluid pump to pump the PD fluid during the patient drain at the applied negative pressure.

In a second aspect of the present disclosure, which may be combined with any other aspect, or portion thereof, the control unit is configured to repeat (i) to (iii) multiple times over the patient drain.

In a third aspect of the present disclosure, which may be combined with any other aspect, or portion thereof, the control unit is configured to repeat (i) to (iii) on a time period basis or on a number of pump strokes basis.

In a fourth aspect of the present disclosure, which may be combined with any other aspect, or portion thereof, the PD fluid pump is pneumatically actuated and the pressure sensor is associated with a pneumatic line positioned and arranged to deliver negative pneumatic pressure to the PD fluid pump.

In a fifth aspect of the present disclosure, which may be combined with any other aspect, or portion thereof, the control unit is configured to accumulate known volume strokes by the PD fluid pump and/or employ an ideal gas law algorithm in determining the flowrate of the PD fluid pumped during the patient drain.

In a sixth aspect of the present disclosure, which may be combined with any other aspect, or portion thereof, the PD fluid pump is a peristaltic pump, a piston pump, or a pressure chamber pump, and wherein the pressure sensor is associated with the patient line.

In a seventh aspect of the present disclosure, which may be combined with any other aspect, or portion thereof, the control unit is configured to use an output from a flow meter associated with the patient line and/or accumulate known volume revolutions by the peristaltic pump or accumulate known volume strokes by the piston pump in determining the flowrate of the PD fluid pumped during the patient drain.

In an eighth aspect of the present disclosure, which may be combined with any other aspect, or portion thereof, the control unit is configured to use an output from a scale for the pressure chamber pump in determining the flowrate of the PD fluid pumped during the patient drain.

In a ninth aspect of the present disclosure, which may be combined with any other aspect, or portion thereof, the control unit is configured to know the flowrate, which is a commanded flowrate.

In a tenth aspect of the present disclosure, which may be combined with any other aspect, or portion thereof, the control unit is configured to determine the applied negative pressure $P_{c\ setpoint}$ by subtracting the pressure drop from an acceptable patient pressure $P_{ac}$, namely, $P_{c\ setpoint}=P_{ac}-\Delta P_{tube}(Q)$, assuming pressure drop is expressed as a positive value.

In an eleventh aspect of the present disclosure, which may be combined with any other aspect, or portion thereof, the acceptable patient pressure is a pressure that will not cause patient drain pain.

In a twelfth aspect of the present disclosure, which may be combined with any other aspect, or portion thereof, a head height delta between the peritoneal cavity of a patient and the PD fluid pump is taken into account, such that the applied negative pressure $P_{c\ setpoint}=P_{ac}+P_{head}-\Delta P_{tube}(Q)$, wherein $P_{head}$ is determined by $\rho\times g\times\Delta h$.

In a thirteenth aspect of the present disclosure, which may be combined with any other aspect, or portion thereof, the control unit is configured to determine the pressure drop using an algorithm that takes into account the determined or known flowrate, at least one characteristic of the patient line, and at least one characteristic of the PD fluid.

In a fourteenth aspect of the present disclosure, which may be combined with any other aspect, or portion thereof, the at least one characteristic of the patient line includes a patient line length, a patient line inner diameter, and a patient line surface roughness.

In a fifteenth aspect of the present disclosure, which may be combined with any other aspect, or portion thereof, the at least one characteristic of the PD fluid includes PD fluid density, PD fluid viscosity, PD fluid composition and PD fluid temperature.

In a sixteenth aspect of the present disclosure, which may be combined with any other aspect, or portion thereof, the algorithm is dependent on whether the PD fluid flowrate is laminar or turbulent.

In a seventeenth aspect of the present disclosure, which may be combined with any other aspect, or portion thereof, the algorithm further takes into account a head height delta between the peritoneal cavity of a patient and the PD fluid pump.

In an eighteenth aspect of the present disclosure, which may be combined with any other aspect, or portion thereof, the control unit is configured to determine the pressure drop using a lookup table that correlates pressure drop and PD fluid flowrate.

In a nineteenth aspect of the present disclosure, which may be combined with any other aspect, or portion thereof, the control unit is configured to determine the applied negative pressure by taking into account a head height delta between the peritoneal cavity of a patient and the PD fluid pump, and wherein the control unit is configured to retake into account a head height delta between the peritoneal cavity of the patient and the PD fluid pump when (i) the pressure sensor detects a threshold unintended PD fluid pressure change or (ii) the control unit determines that a threshold unintended PD fluid flowrate has occurred.

In a twentieth aspect of the present disclosure, which may be combined with any other aspect, or portion thereof, the control unit is configured to determine the head height delta between the peritoneal cavity of the patient and the PD fluid pump by slowing or stopping the PD fluid pump at least one time and reading a resulting output from the pressure sensor.

In a twenty-first aspect of the present disclosure, which may be combined with any other aspect, or portion thereof, the control unit is configured to use the sensed negative pressure from the pressure sensor as feedback in a pressure control routine to cause the PD fluid pump to pump the PD fluid during the patient drain at the applied negative pressure.

In a twenty-second aspect of the present disclosure, which may be combined with any other aspect, or portion thereof, a method for minimizing patient drain pain in a peritoneal dialysis (PD) system is disclosed. The method includes: (i) determining or knowing, by a control unit of the PD system, a flowrate of PD fluid pumped by a PD fluid pump of the PD system during a patient drain, wherein a patient line of the PD system receives used PD fluid; (ii) determining, by the control unit, an applied negative pressure at which the PD fluid pump is to pump the PD fluid during the patient drain, the applied pressure based on a pressure drop corresponding to the determined or known flowrate; and (iii) causing, based on negative pressure associated with the PD fluid and sensed by a pressure sensor of the PD system, the PD fluid pump to pump the PD fluid during the patient drain at the applied negative pressure.

In a twenty-third aspect of the present disclosure, which may be combined with any other aspect, or portion thereof, one or more iterations of (i) to (iii) nay be performed by the control unit multiple times over the patient drain. Furthermore, the one or more iterations are performed on a time period basis or on a number of pump strokes basis.

In a twenty-fourth aspect of the present disclosure, which may be combined with any other aspect, or portion thereof, the method further comprises: accumulating known volume strokes by the PD fluid pump; or employing an ideal gas law algorithm in determining the flowrate of the PD fluid pumped during the patient drain.

In a twenty-fifth aspect of the present disclosure, which may be combined with any other aspect, or portion thereof, the PD fluid pump is a peristaltic pump, a piston pump, or a pressure chamber pump. The pressure sensor is associated with the patient line. The flowrate of the PD fluid pumped during the patient drain is determined based on one or more of: an output from a flow meter associated with the patent line, an accumulated known volume revolutions by the peristaltic pump, an accumulate known volume strokes by the piston pump, or an output from a scale for the pressure chamber pump.

In a twenty-sixth aspect of the present disclosure, which may be combined with any other aspect, or portion thereof, the applied negative pressure, $P_{c\ setpoint}$, is determined by subtracting the pressure drop from an acceptable patient pressure $P_{ac}$, namely, $P_{c\ setpoint}=P_{ac}-\Delta P_{tube}(Q)$, assuming the pressure drop is expressed as a positive value.

In a twenty-seventh aspect of the present disclosure, which may be combined with any other aspect, or portion thereof, the pressure drop is determined using an algorithm that takes into account the determined or known flowrate, at least one characteristic of the patient line, and at least one characteristic of the PD fluid.

In a twenty-eighth aspect of the present disclosure, which may be combined with any other aspect, or portion thereof, the pressure drop is determined using a lookup table that correlates pressure drop and PD fluid flowrate.

In a twenty-ninth aspect of the present disclosure, which may be combined with any other aspect, or portion thereof, the applied negative pressure is determined by taking into account a head height delta between the peritoneal cavity of a patient and the PD fluid pump. The method further comprises: retaking into account a head height delta between the peritoneal cavity of the patient and the PD fluid pump when (i) a threshold unintended PD fluid pressure change is detected or (ii) a threshold unintended PD fluid flowrate has occurred.

In a thirtieth aspect of the present disclosure, which may be combined with any other aspect, or portion thereof, the head height delta between the peritoneal cavity of the patient and the PD fluid pump is determined by slowing or stopping the PD fluid pump at least one time and reading a resulting output from the pressure sensor.

In a thirty-first aspect of the present disclosure, which may be combined with any other aspect, or portion thereof, the method further comprises: using, by the control unit, the sensed negative pressure from the pressure sensor as feedback in a pressure control routine to cause the PD fluid pump to pump the PD fluid during the patient drain at the applied negative pressure.

In a thirty-second aspect of the present disclosure, which may be combined with any other aspect, or portion thereof, any of the features, functionality and alternatives described in connection with any one or more of FIGS. 1 to 4B may be combined with any of the features, functionality and alternatives described in connection with any other of FIGS. 1 to 4B.

In light of the above aspects and present disclosure set forth herein, it is an advantage of the present disclosure to provide a system and method for an automated peritoneal dialysis ("APD") cycler that minimizes patient drain pain.

It is another advantage of the present disclosure to provide a system and method for an APD cycler that increases patient drain flowrate and reduces patient drain time, increasing available patient dwell time and/or shortening overall treatment time.

It is a further advantage of the present disclosure to provide a system and method for an APD cycler that allows for a less expensive patient line and corresponding disposable set.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
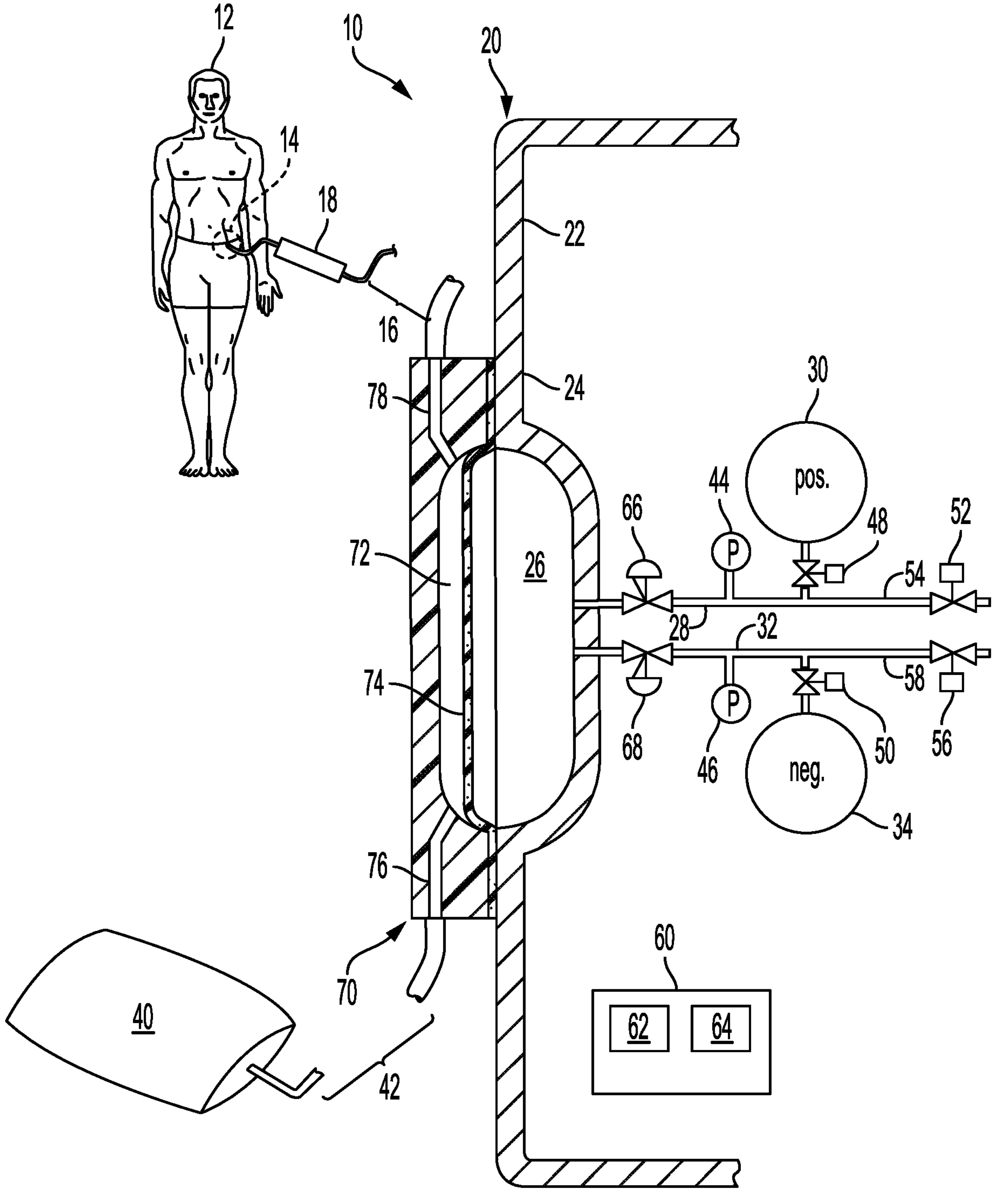
FIG. 1 is a sectioned schematic view of one embodiment for an APD system having the methodology for minimizing patient drain pain of the present disclosure.

Referring now to the drawings and in particular to FIG. 1, an example system 10 including the patient drain pain reduction methodology of the present disclosure is illustrated. System 10 includes a dialysis machine 20, such as an APD machine, operating a medical fluid handling device 70, such as a dialysis fluid cassette. PD machine 20 includes a housing 22 defining a pump interface 24 having a pump actuator or pump actuation area 26 for actuating medical fluid handling device 70. Pump actuation area 26 in the illustrated embodiment is actuated pneumatically via a positive pneumatic line 28 extending from a positive pneumatic source 30 to perform a pump-out or discharge stroke, e.g., to push (i) fresh, heated dialysis fluid to a peritoneal cavity 14 of patient 12 via a patient line 16 and patient transfer set 18, (ii) fresh dialysis fluid to a heating container (not illustrated) to be heated to body temperature, e.g., 37° C., by a dialysis fluid heater (not illustrated), or (iii) used dialysis fluid to a drain. Pump actuation area 26 in the illustrated embodiment is actuated pneumatically via a negative pneumatic line 32 extending from a negative pneumatic source 34 to perform a pump-in or draw stroke, e.g., to pull (i) fresh dialysis fluid from a dialysis fluid source 40 through a supply line 42, (ii) fresh, heated dialysis fluid from the heating container (not illustrated), or (iii) used dialysis fluid from the peritoneal cavity 14 of patient 12 via patient line 16 and transfer set 18.

Patient line 16 may be from three to seven meters long, e.g., approximately 4.5 or 6.7 meters, and have an internal diameter of, for example, three to four millimeters. In the equations discussed herein, it is assumed that different disposable patient lines 16 have and provide the same basic behavior from treatment to treatment.

PD machine 20 also provides a pressure sensor 44 for measuring positive pneumatic pressure in positive pneumatic line 28 and a pressure sensor 46 for measuring negative pneumatic pressure in negative pneumatic line 32. PD machine 20 further includes plural electrically operated pneumatic valves, e.g., valves 48, 50, 52 and 56. Pneumatic valve 48 is positioned in positive pneumatic line 28 to selectively allow positive pressure from source 30 to reach pump actuation area 26. Pneumatic valve 50 is positioned in negative pneumatic line 32 to selectively allow negative pressure from source 34 to reach pump actuation area 26. A vent valve 52 is provided in a vent line 54 in communication with positive pneumatic line 28 to selectively vent positive pressure in line 28 and pump actuation area 26 to atmosphere. A second vent valve 56 is provided in a vent line 58 in communication with negative pneumatic line 32 to selectively vent negative pressure in line 32 and pump actuation area 26 to atmosphere. In an alternative embodiment, a single vent valve and line may be provided to vent both positive and negative pressure from pump actuation area 26 to atmosphere.

FIG. 1 further illustrates that PD machine 20 includes a positive pneumatic pressure regulator 66, e.g., a variable orifice valve, located along positive pneumatic line 28, and a negative pressure regulator 68, e.g., a variable orifice valve, located along negative pneumatic line 32. Positive pneumatic pressure regulator 66 sets the positive pneumatic pressure delivered to pump actuation area 26 to a desired and controlled level, which is also the pressure of fresh or used PD fluid pumped out of dialysis fluid cassette 70. Negative pneumatic pressure regulator 68 sets the negative pneumatic pressure drawn at pump actuation area 26 to a desired and controlled level, which is also the pressure of fresh or used PD fluid pumped into dialysis fluid cassette 70. In an alternative embodiment, PD machine 20 may be configured pneumatically such that a single pressure regulator, e.g., variable orifice valve, operates at different times as a positive pneumatic pressure regulator and a negative pneumatic pressure regulator.

Pressure sensors 44 and 46, pneumatic valves 48, 50, 52 and 56, and variable orifice valves or regulators 66 and 68 either output to or are under the control of a control unit 60 of PD machine 20. Control unit 60 in the illustrated embodiment includes one or more processor 62 and one or more memory 64. Control unit 60 may have any one or more of a master controller, safety controller, video controller, and/or sub- or delegate controller. Control unit 60 receives pressure readings from pressure sensors 44 and 46 and selectively opens and closes pneumatic solenoid valves 48, 50, 52 and 56 at programmed times or stages. Control unit 60 uses the output of pressure sensors 44 and 46, respectively, in a pressure control routine to control variable orifice valves or regulators 66 and 68 so as to deliver positive and negative pneumatic pressure at a desired or commanded level. It should be appreciated that control unit 60 may operate with additional pressure sensors, temperature sensors, valves, and the PD fluid heater, which are not illustrated to simplify FIG. 1.

In the illustrated embodiment of FIG. 1, medical fluid handling device or disposable cassette 70 is provided with a pump actuation chamber 72 that mates with pump actuation area 26 to form an overall pumping chamber. Medical fluid handling device 70 in the illustrated embodiment includes a flexible membrane, diaphragm or sheet 74, which may be sized to fit pump actuation chamber 72 or be sized to cover a whole side of medical fluid handling device 70 (as illustrated), wherein a portion of the membrane 74 covers pump actuation chamber 72, and wherein such portion may be at least substantially flat or be pre-domed or pre-shaped to fit into one or both pump actuation area 26 and pump actuation chamber 72. Flexible membrane 74 (or separate membranes) may also cover and be used to actuate medical fluid valves (not illustrated), such as (i) a fluid valve positioned and arranged to selectively allow medical fluid to flow from fluid source 40, through supply line 42 and a supply channel 76 of medical fluid handling device 70 to pump actuation chamber 72 and (ii) a fluid valve positioned and arranged to selectively allow medical fluid to flow from pump actuation chamber 72 through a patient channel 78 of medical fluid handling device 70, through patient line 16 and patient transfer set 18 to peritoneal cavity 14 of patient 12. It should be appreciated that medical fluid handling device 70 may have additional fluid valves, e.g., additional fluid valves for an additional pump actuation chamber 72 (operating in an alternating manner to provide more continuous flow) and additional fluid valves for multiple supply lines 42, a fluid heater line, and/or a drain line, which are not illustrated to simplify FIG. 1.

Control unit 60 causes negative pressure from source 34 to be applied to flexible membrane 74 to pull the sheet against the wall of pump actuation area 26 to correspondingly pull fresh or used PD fluid into pump actuation chamber 72. To do so, control unit causes valves 48, 52 and 56 to be closed and valve 50 to be open. During the filling of pump actuation chamber 72, pressure sensor 46 measures negative pumping pressure, which is used as feedback in a pressure control routine to set the level of negative pneumatic pressure applied at pump actuation area 26 via negative pressure regulator 68.

Control unit 60 causes positive pressure from source 30 to be applied to flexible membrane 74 to push the sheet against the wall of pump actuation chamber 72 to correspondingly push fresh or used PD fluid from pump actuation chamber 72. To do so, control unit causes valves 50, 52 and 56 to be closed and valve 48 to be open. During the discharge of pump actuation chamber 72, pressure sensor 44 measures positive pumping pressure, which is used as feedback in a pressure control routine to set the level of positive pneumatic pressure applied at pump actuation area 26 via positive pressure regulator 66.

Control unit 60 is able to determine the flowrate of fresh and used PD fluid pumped by PD machine 20 of system 10 in at least one of a plurality of different ways. In one way, the fixed volumes of pump actuation area 26 and pump actuation chamber 72 collectively form a known full stroke volume. Control unit 60 counts the number of full strokes delivered, multiplies the count by the known full stroke volume, and divides the result by the corresponding amount of time needed to perform the number of full strokes delivered to determine a local or current PD fluid flowrate.

Alternatively or additionally, control unit 60 takes before and after fill or discharge stroke pressure measurements and uses an ideal gas law algorithm, as is known in the art, to determine a resulting volume of fresh or used PD fluid pulled into or discharged from pump actuation chamber 72. To do so, PD machine 20 may provide positive and negative known and fixed volume reference chambers (not illustrated), which may be pneumatically connected to positive and negative vent lines 54 and 58, respectively. Control unit 60 may then add consecutive fill or discharge stroke volumes determined by the ideal gas law algorithm and divide the sum by the corresponding amount of time needed to perform the consecutive fill or discharge strokes to determine a local or current PD fluid flowrate. The ideal gas law algorithm method of determining local or current flowrate is advantageous because full stokes of diaphragm or sheet 74 through pump actuation area 26 and pump actuation chamber 72 are not required. Partial strokes may be performed and taken into account in determining local or current flowrate.

It should be appreciated that it is likely that PD machine 20 provides two pump actuation areas 26 and pump actuation chambers 72, which operate in an alternating manner (one filling while the other discharging), so that the flowrate of fresh or used PD fluid is for the most part continuous.

As discussed herein, applying a constant negative pressure during a patient drain may lead to patient drain pain during periods of low flowrate. Low effluent or used PD fluid flowrate may occur anytime during a patient drain due for example to a partial occlusion of patient line 16. Low drain flowrate may also arise at the end of a patient drain. Effluent is in less supply and the peritoneal membrane may start to enclose around the catheter, causing the pressure drop between the inside of the patient's indwelling catheter and peritoneal cavity 14 to increase, decreasing drain flow. The lowered drain flowrate causes the pressure drop in patient line 16 to decrease. If the applied negative pressure were to remain at, e.g., −9 kPa (−1.3 psig), the pressure that the patient sees increases negatively, which may ultimately lead to drain pain.

To combat drain pain, control unit 60 of APD system 10 of the present disclosure is programmed with the ability to adjust at least an applied negative pressure (and an applied positive pressure), as discussed above, and to measure at least a patient drain flowrate (and a patient fill flowrate), as discussed above. During the patient drain, control unit 60 is programmed to periodically (e.g., once every set time period, such as five to sixty seconds, or once every set number of pump strokes, such as one to five strokes) determine the current flowrate, e.g., in the manner described above. Control unit 60 alternatively periodically looks to update a commanded flowrate. Control unit 60 in either scenario uses the current flowrate to determine a corresponding pressure drop along patient line 16. The corresponding pressure drop may be determined using the following equations.

The corresponding pressure drop through patient line 16 may be determined beginning with a friction head height equation, see Frank M. White, Fluid Mechanics, 2011:

$$h_f = f\frac{L}{d}\frac{V^2}{2g} = \frac{8\text{fL}Q^2}{\pi^2 g d^5}$$

The term $h_f$ is the friction head height in meters ("m"), $f$ is the Darcy friction factor (discussed below), L is the length of patient line 16 in meters, d is the inner diameter of patient line 16 in meters, V is the velocity of the PD fluid in meters/second (equals the determined flowrate divided by internal area of patient line 16), g is the earth's gravity in m/sec$^2$, Q is the determined, current volumetric PD fluid flowrate in m$^3$/sec.

The following equation may be used to derive pressure drop from head height:

$$h_f = \frac{1000\Delta P}{\rho g} \rightarrow \Delta P = \frac{h_f \rho g}{1000},$$

where ΔP is the pressure drop in kPa, ρ is the density of the PD fluid in kilograms ("kg")/m$^3$. The two equations combine to yield:

$$\Delta P = \frac{8f\rho L Q^2}{1000\pi^2 d^5}$$

The Darcy friction factor is dependent on Reynolds number ("Re"), which is a dimensionless value used in flow dynamics, and the relative roughness (ε/d) of the inner diameter of patient line 16, where ε is the patent line's effective roughness height in meters and d is the inner diameter of patient line 16 in meters. For patient line 16 flows during laminar conditions, the Darcy factor may be calculated using the owing equation:

$$f_{lam} = \frac{64}{Re}$$

The Reynolds number may be calculated with the following equation:

$$Re = \frac{\rho V d}{\mu},$$

where μ is the dynamic viscosity of the PD fluid in kg/m×s. If the flow in patient line 16 is turbulent, i.e., Reynolds numbers above 4000, a turbulent model for the Darcy friction factor is applied. For full stable turbulent flow, the Colebrook-White equation may be used to calculate the friction factor in the turbulent regime:

$$\frac{1}{\sqrt{f}} = -2.0\log\left(\frac{\frac{\epsilon}{d}}{3.7} + \frac{2.51}{Re\sqrt{f}}\right)$$

The above equation may be solved numerically or may be approximated using the following equation (Haaland):

$$\frac{1}{\sqrt{f}} \approx -1.8\log\left(\left(\frac{\frac{\epsilon}{d}}{3.7}\right)^{1.11} + \frac{6.9}{Re}\right)$$

The Haaland equation, among others, has been simulated for Reynolds numbers in the range of 2300 to 100000, see Jukka Kiijärvi, Lunowa Fluid Mechanics Paper 11027 Jul. 29 2011. The Haaland equation is said to yield errors in the Darcy friction factor $f$ of about 2%, which is acceptable especially given that the dimensions and surface qualities of patient line 16 are consistent from treatment to treatment. Assuming patient line 16 is made of polyvinyl chloride ("PVC"), the surface roughness ε for a drawn tube in PVC (and other drawn tube materials) may be taken to be 0.0015 mm.

Flow in patient line 16 having a Reynolds number between 2300 and 4000 is considered transient. The friction factor here will be somewhere in between $f_{lam}$ and $f_{turbulent}$.

As shown above, pressure drop ΔP may be determined knowing the length, inner diameter and surface roughness of patient line 16, the dynamic viscosity and density of the PD fluid (e.g., based on PD fluid composition, such as glucose level), and the determined local or current PD fluid flowrate. PD fluid temperature may also be taken into account. The equations above (or at least some of them) may be stored in one or more memory 64 and accessed by one or more processor 62 of control unit 60 to calculate a local or current pressure drop ΔP based on a newly determined flowrate. It should be appreciated that the current flowrate may not need to be calculated, e.g., based on stroke volume and stroke count, and may instead be a known and commanded flowrate set in memory 64 of control unit 60. The equations stored in memory for calculating pressure drop ΔP here may use a flowrate currently commanded by control unit 60.

The pressure drop ΔP corresponding to a newly determined (or currently commanded) flowrate may be determined alternatively using one or more lookup table stored in memory 64 that correlates pressure drop to measured flowrate. The lookup table may be populated using the equations discussed herein. A sample lookup table for common PD fluids and typical PD fluid flowrates is shown in Table 1, where the populated values are pressure drop ΔP values:

TABLE 1

| PD solution | Flowrates (ml/min) 50 | 100 | 150 | 250 | 350 |
|---|---|---|---|---|---|
| Dianeal ™ 1.36% | 0.63 | 1.26 | 1.89 | 3.15 | 8.34 |
| Dianeal ™ 2.26% | 0.65 | 1.29 | 1.94 | 3.23 | 8.42 |

TABLE 1-continued

| PD solution | Flowrates (ml/min) 50 | 100 | 150 | 250 | 350 |
|---|---|---|---|---|---|
| Dianeal ™ 3.86% | 0.67 | 1.34 | 2.01 | 3.35 | 8.55 |
| Extraneal ™ | 1.03 | 2.05 | 3.08 | 5.13 | 7.18 |

Figure 2:
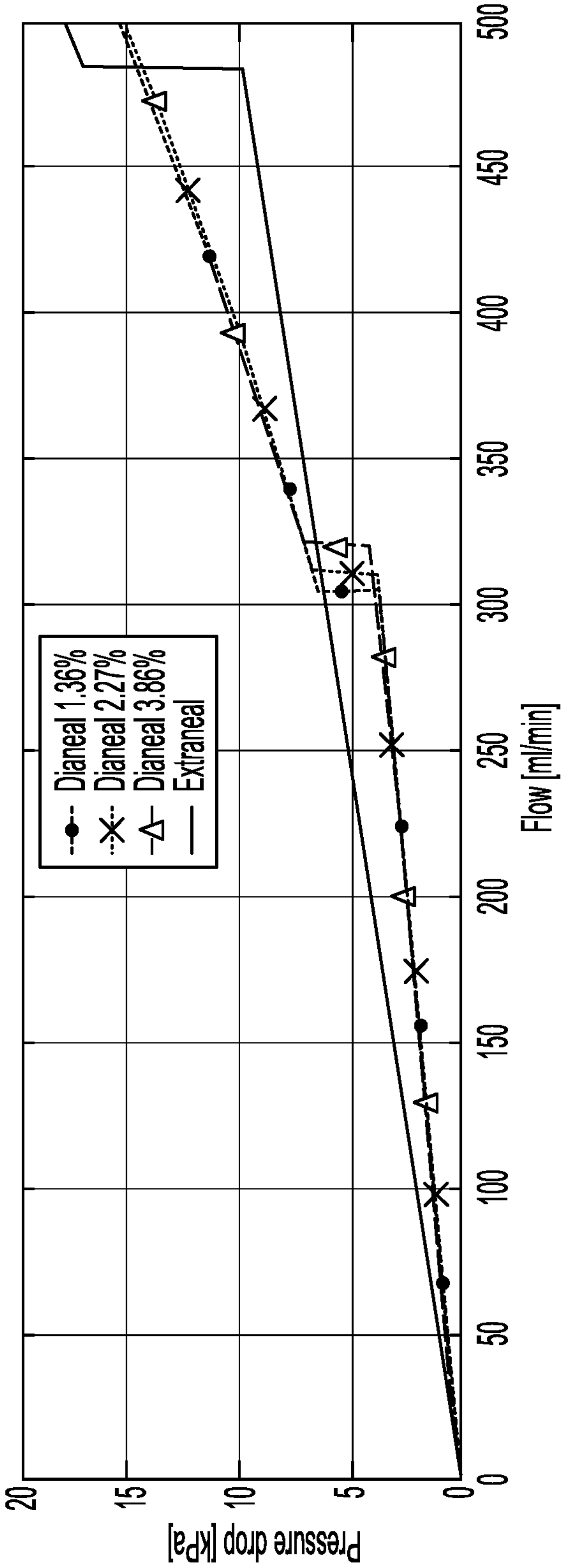
FIG. 2 is a plot of patient line pressure drop versus drain flowrate for a plurality of different types of PD fluids drained at typical APD flowrates.

FIG. 2 is essentially a plot of Table 1 showing how pressure drop ΔP varies as a function of flowrate for four different types of PD fluids, which have varying densities and viscosities based on their different chemical makeups. Each PD fluid consistently shows that as flowrate increases, pressure drop ΔP increases. FIG. 2 illustrates that at high flowrates, almost all negative pressure created by PD machine 20 is expended over the length of patient line 16. The pressure in the patient's peritoneal cavity 14 is here accordingly close to its normal pressure, e.g., slightly above atmospheric pressure. When control unit 60 detects that drain flowrate is about 350 ml/min, control unit 60 can cause negative drain pressure to be applied at around −9 kPa (−1.3 psig) as discussed herein. When control unit 60 detects that the flowrate drops to, e.g., 250 ml/min, control unit 60 lowers the commanded negative drain pressure to about −5 kPa (−0.73 psig). When the drain flowrate drops further, control unit 60 needs to further reduce the commanded negative pressure to avoid the patient potentially experiencing drain pain.

It should be appreciated that Table 1 and FIG. 2 illustrate an example in which PD machine 20 is at roughly the same head height as the patient's peritoneal cavity. In situations in which the head heights are different in such a way to work against the ability of the PD machine 20 to remove effluent from the patient (where PD machine 20 is located elevationally above the patient), the −9 kPa (−1.3 psig) may be needed even at lower flowrates. To establish flowrate initially, taking head height into account, control unit 60 is in one embodiment programmed to cause pump actuation area 26 of the PD fluid pump to begin pulling and draining effluent at a lower flowrate. Control unit 60 determines the resulting flowrate and thus knows whether the patient is relatively full and the flowrate is high or that the flowrate is lower for some reason, e.g., the patient is not full. If the patient is relatively full and the flowrate is high, control unit 60 then increases the negative drain pressure using the equations discussed herein to drain the patient more quickly while still avoiding patient drain pain.

Knowing the pressure drop for the current flowrate, control unit 60 is in one embodiment programmed to cause the negative patient drain pumping pressure to be adjusted so that the resulting effluent pressure at the patient's peritoneal cavity 14 is at a level that will likely not cause drain pain, e.g., at or around the standing still, patient full pressure of 12 cmH2O (≈8.8 mmHg, 1.18 kPa, 0.17 psig). By periodically checking the current patient drain flowrate (or periodically looking to update a flowrate commanded by control unit 60) and updating the applied negative patient drain pressure, control unit 60 of present system 10 maintains the natural (patient full) patient pressure over the course of each patient drain of a PD treatment. The overall effect is to reduce, and perhaps greatly reduce the likelihood of patient drain pain.

Control unit 60 in an alternative embodiment is programmed to begin a patient drain by applying a low negative drain pressure, such as −1 kPa (−0.15 psig). After, if control unit 60 detects that the flowrate is above a first threshold, for example, 75 ml/min, then the commanded negative pressure is increased by an incremental amount, e.g., −2 kPa (−0.29 psig). If control unit 60 instead detects that the flowrate is below a second threshold, for example, below 50 ml/min, then control unit maintains the negative pressure at −1 kPa (−0.15 psig). Control unit 60 may command the −2 kPa (−0.29 psig) negative pressure to be used over the linear ranges in FIG. 2, e.g., below 300 ml/min. When the flowrate increases to or over the linear range breakpoint, e.g., 300 ml/min, or a minimum negative pressure at peritoneal cavity 14 is reached, control unit 60 may turn to using the stored equations discussed above.

Control unit 60 in the present alternative embodiment is programmed such that at a maximum patient drain flowrate (e.g., maximum commanded flowrate), the pressure at the patient's peritoneal cavity 14 or abdominal cavity ("ac") is calculated and used as a setpoint for the rest of the drain phase. Such pressure may be called $P_{ac}$. When the patient drain flowrate starts to drop, control unit 60 calculates the pressure drop $\Delta P_{tube}(Q)$ for the current flowrate (or uses a lookup table). Control unit 60 then calculates the applied or setpoint pressure ($P_{c\ setpoint}$) by summing the pressure drop and the pressure $P_{ac}$, such that $P_{c\ setpoint}=P_{ac}-\Delta P_{tube}(Q)$ (assuming pressure drop is expressed as a positive value).

In an example using values from Table 1, suppose the maximum flowrate is 350 ml/min at an applied −9 kPa using (using Dianeal™ 2.26%). The pressure at the patient's peritoneal cavity 14, $P_{ac}$, is accordingly −9 kPa+8.42 kPa=−0.58 kPa, wherein −0.58 kPa is accordingly used as the allowed patient pressure for the remainder of treatment, that is, the patient pressure will remain at or about −0.58 kPa throughout the remainder of the patient drain. The applied pressure at PD machine 20 ($P_{c\ setpoint}$) is varied by control unit 60 depending on measured or commanded flowrate. $P_{c\ setpoint}$ will start at −9 kPa and slowly become less negative as the patient drain flowrate (and corresponding drop) falls. Patient pressure is accordingly kept constant (or almost constant) and pain free.

The above equation again assumes that PD machine 20 is at the same elevation as the patient's peritoneal cavity and that delta head height is therefore zero. Expanding the above equation to take into account head height, the equation may become $P_{c\ setpoint}=P_{ac}+P_{head}-\Delta P_{tube}(Q)$, where $P_{head}$ is determined by $\rho\times g\times\Delta h$, and where $\Delta h$ expresses where the patient's peritoneal cavity is located in relation to PD machine 20. For example, if the peritoneal cavity is located 0.5 meter ("m") below PD machine 20, then h=−0.5 m and $P_{head}$ is thereby roughly −5 kPa. The resulting setpoint pressure is, at a flow rate of 250 ml/min, $P_{c\ setpoint}=P_{ac}+(-5)-4=P_{ac}-9$ kPa. If the patient is instead located 0.5 m above PD machine 20, the resulting setpoint pressure at the same flowrate is $P_{c\ setpoint}=P_{ac}+5-4=P_{ac}+1$ kPa (here, the head height helps draining the patient).

The above examples illustrate that system 10 of the present disclosure takes into account the relative height between the location of pump actuator or pump actuation area 26 of PD machine 20 and the location of peritoneal cavity 14 of patient 12 illustrated in FIG. 1. For example, a 0.5 meter head height difference where (i) pump actuator or pump actuation area 26 is below peritoneal cavity 14 allows PD machine 20 to lessen its suction pressure by a delta of about 5 kPa, and (ii) pump actuator or pump actuation area 26 is above peritoneal cavity 14 allows PD machine 20 to increase its suction pressure by a delta of about 5 kPa. The pressure experienced at peritoneal cavity 14 is the same in both cases.

Figure 4A:
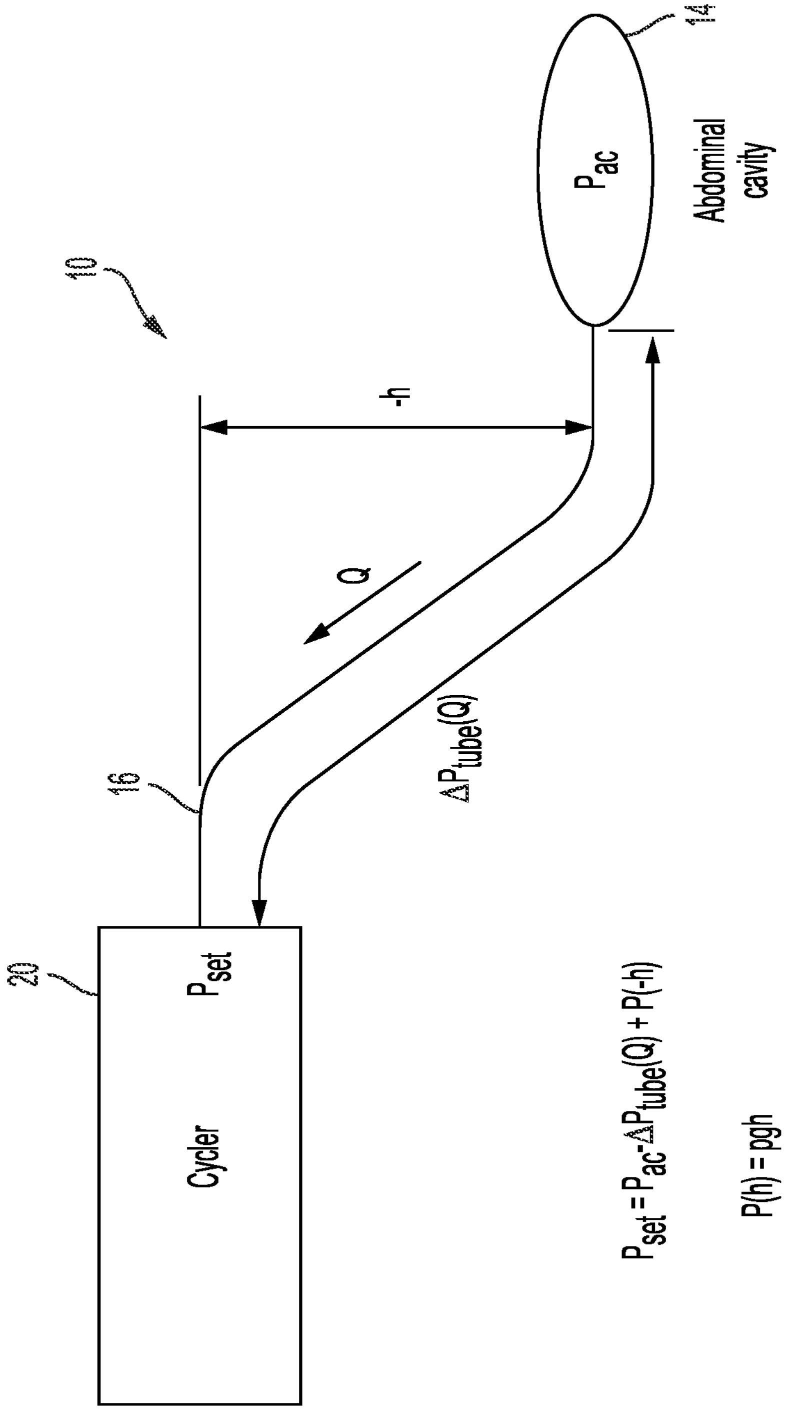
FIGS. 4A and 4B are schematic views of the PD machine, patient and patient line illustrating how patient head height is taken into account when determining a dialysis machine negative pressure drain setpoint.
Figure 4B:
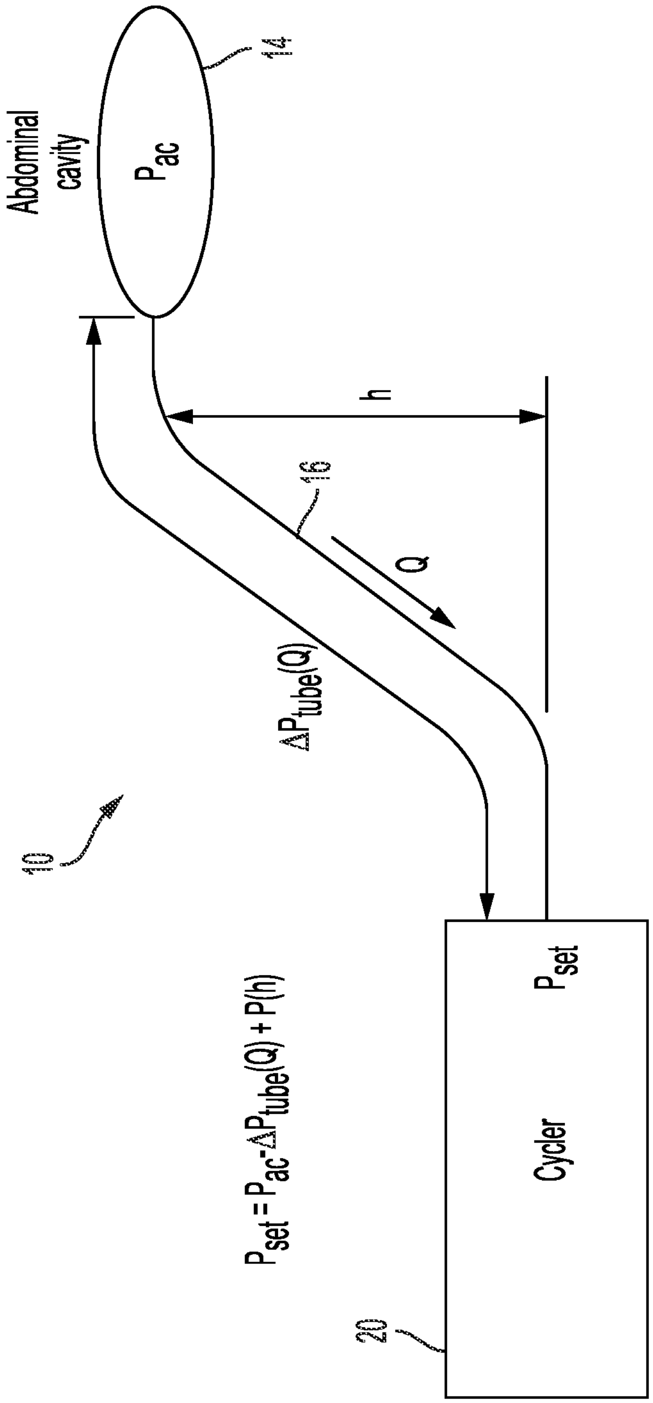

FIGS. 4A and 4B illustrate an embodiment for taking into account patient head height in determining a resulting drain setpoint pressure, $P_{c\ setpoint}$. FIGS. 4A and 4B schematically illustrate that PD machine 20 of system 10 includes a patient line 16 that connects to peritoneal cavity 14 of patient 12. In FIG. 4A, the peritoneal or abdominal cavity 14 of patient 12 is located a distance −h below PD machine 20. PD machine 20 accordingly has to pull against the patient head height delta and supply additional negative drain pressure. The negative drain setpoint pressure is accordingly $P_{c\ setpoint}=P_{ac}-\Delta P_{tube}(Q)+P(-h)$, where $P(h)=\rho\times g\times\Delta h$. In FIG. 4B, the peritoneal or abdominal cavity 14 of patient 12 is located a distance +h above PD machine 20. PD machine 20 is accordingly aided by the patient head height delta in pulling effluent from the patient during drain. The negative setpoint drain pressure is here $P_{c\ setpoint}=P_{ac}-\Delta P_{tube}(Q)+P(h)$, where again $P(h)=\rho\times g\times\Delta h$.

To determine the head height delta, PD machine 20 of system 10 in an embodiment asks patient 12 prior to treatment to enter (i) whether the patient's stomach area is above or below pump actuator or pump actuation area 26 (a horizontal line may be placed on the front of PD machine housing 22 as a reference) and (ii) by how much (e.g., entered in centimeters, meters, inches or feet). Control unit 60 of PD machine 20 of system 10 alternatively or additionally determines the head height delta by taking a pressure measurement at pressure sensor(s) 44, 46 (or an inline pressure sensor for an electromechanical pump actuator 26) when the PD fluid flowrate is zero. Here, if the patient is above the PD machine 20, the pressure measurement will be positive. If the patient is below the PD machine 20, the pressure measurement will be negative. The magnitude of the negative or positive pressure measurement indicates how far above or below, respectively, the patient is from PD machine 20.

If while pumping, (i) pressure sensor(s) 44, 46 (or other one or pressure sensor) sense (or senses) a meaningful or threshold unintended PD fluid pressure change or (ii) control unit 60 determines that a meaningful or threshold unintended PD fluid flowrate change has occurred, control unit 60 may stop the operation of pump actuator or pump actuation area 26, so that the PD fluid flowrate goes to zero, and retake the head height determination pressure measurement. Control unit 60 then adjusts the pressure setpoint based on the new head height delta determined. In an alternative embodiment, control unit 60 only slows the PD fluid flowrate (e.g., one or more time) in an attempt to distinguish between a change in head height delta and an occlusion of patient line 16. If the sensed pressure remains constant despite the PD fluid flowrate change (or changes in a way that is not expected for a change in patent head height, then control unit 60 determines that the original sensed pressure change is due to an occlusion, such as an occlusion due to omental wrapping, catheter migration/blockage, patient 12 moving to block patient line 16 (FIG. 1), each of which results in a changed drain profile. If the sensed pressure changes as a function of the PD fluid flowrate change, then control unit 60 determines that the original sensed pressure change is due to a change in head height between peritoneal cavity 14 and pump actuation area 26. Control unit 60 then adjusts the pressure setpoint based on the new head height delta determined via the one or more slowing of the PD flowrate and the corresponding measured pressure(s). Viewing FIG. 1, it should be appreciated that placing one or more pressure sensor along patient channel 78 just upstream from patient line 16 would allow patient head height to be monitored continuously regardless of the type of pumping provided, e.g., piston pumping, pneumatic pumping, peristaltic pumping, etc.

It should be understood that various changes and modifications to the presently preferred embodiments described herein will be apparent to those skilled in the art. It is therefore intended that such changes and modifications be covered by the appended claims. For example, while PD machine 20 has been illustrated as a pneumatically operated PD machine, system 10 may alternatively employ different types of PD fluid pumping (and valving), e.g., peristaltic pumping, piston pump pumping, or pumping using a PD fluid pump having a pressure chamber. Here, control unit 60 of system 10 may employ multiple proportional, integral, differential ("PID") control loops, such as an "inner" control loop and an "outer" control loop, which may be termed a cascaded controller. The inner control loop may for example employ a "stiff" control of PD fluid flowrate. The outer control loop may instead provide a setpoint based on measured pressure. The overall compliance of the length of patient line 16, etc., dampens the oscillations of the stiffly controlled electromechanical pumps (e.g., piston or peristaltic), allowing an even pressure to be delivered at the patient.

Figure 3:
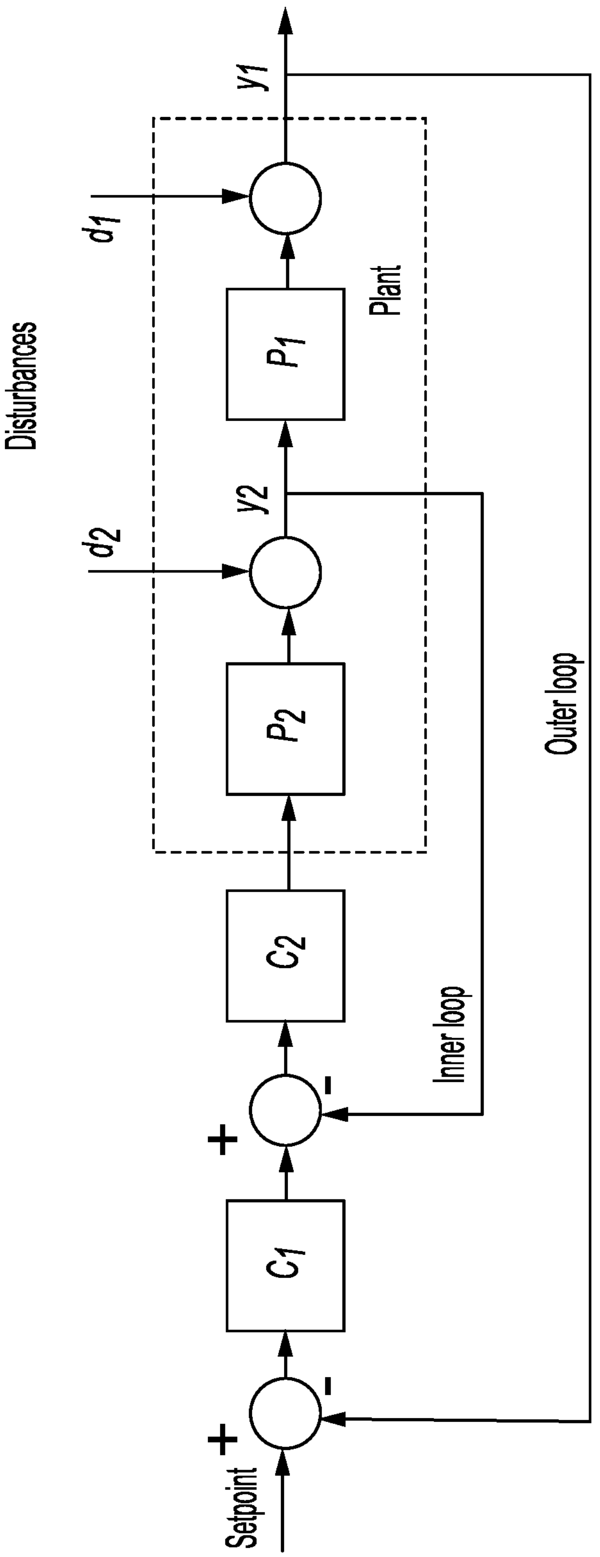
FIG. 3 is a schematic view illustrating one possible control hierarchy for controlling electromechanical pumps (e.g., piston or peristaltic) so as to manage pressure at the patient according to the present disclosure.

FIG. 3 illustrates an example of the multiple control loops that may be used to control electromechanical pumps (e.g., piston or peristaltic) so as to manage pressure at the patient as described herein to reduce or eliminate drain pain. FIG. 3 illustrates that the electromechanical pump control scheme includes an inner loop, which may be termed a fast control loop, and which includes $C_2$ and process $P_2$. $C_2$ is the electromechanical pump motor driver (electrical circuit), which inputs a motor shaft revolutions per minute ("RPM") setpoint value. The output of the inner loop from the summation circle with disturbance $d_2$ is $y_2$, which represents PD fluid flow, which in the process $P_2$ of the inner loop for a piston pump may, for example, be taken as 0.5 ml per revolution.

The inner loop of the electromechanical pump control scheme of FIG. 3 is accordingly a direct fast translation between motor shaft RPM to flowrate in ml/min (for an electromechanical pump actuator 26), which takes into account disturbance $d_2$. Disturbance $d_2$ may be any disturbance affecting process $P_2$ of the inner loop. Possible examples include (i) the supply voltage to the motor driver of an electromechanical pump actuator 26 being shifted, e.g., the supply voltage lowering from 24.7 VDC to 23.4 VDC due to the dialysis fluid heater being energized, and (ii) a stroke volume change, e.g., for a peristaltic pump actuator 26 where the pumping tube segment becomes worn over time, such that the stroke volume drops from 1 ml/stroke to 0.9 ml/stroke.

The outer loop of the electromechanical pump control scheme of FIG. 3 controls pressure by providing an RPM setpoint to the inner loop. Process $P_1$ is the outer loop process describing how PD fluid flowrate corresponds to PD fluid pressure, which in one embodiment is filtered by a low pass filter. The low pass filter and the compliance of patient line 16 form process $P_1$, wherein C1 is the controller (e.g., employing PID pressure control) that controls pressure accordingly. Disturbance $d_1$ may be any disturbance affecting process $P_1$ of the outer loop. A possible example here includes PD fluid pressure fluctuations due to patient movement. The initial setpoint in (signal furthest to the left) is a pressure setpoint by the electromechanical pump PD machine or cycler 20. In FIG. 3, the inner loop controls the speed of electromechanical pump actuator 26 (e.g., RPM), which is directly linked to flow (e.g., via fixed stroke volume). The outer loop control pressure, y1, is the output of the overall control arrangement of FIG. 3, which is a function of the effect of the inner loop.

Alternative pumping, e.g., pressure chamber pumping, may also be employed with one or more scale that outputs to control unit 60 so that an amount of fresh PD fluid delivered to, and an amount of used PD fluid pulled from the patient, may be known. A fresh or used PD fluid change in weight may also be divided by a corresponding time duration to determine a current or local fresh or used PD fluid flowrate if desired. In such alternative pumping embodiments, one or more pressure sensor outputting to control unit 60 may be positioned to sense positive and negative PD fluid pressures along patient line 16. The one or more pressure sensor may be a pod type sensor or a strain gauge type sensor that directly contacts patient line 16. PD fluid flowrate may be obtained from a flowmeter associated with patient line 16 and/or by accumulating known volume (for the most part) peristaltic pump revolutions or accumulating known volume piston pump strokes and dividing by a corresponding time duration needed to make such revolutions or strokes.

The invention is claimed as follows:

1. A peritoneal dialysis ("PD") system comprising:

a PD fluid pump;

a patient line for receiving used PD fluid pumped by the PD fluid pump during a patient drain;

a pressure sensor positioned and arranged to sense a negative pressure associated with the PD fluid pumped during the patient drain; and a control unit configured to (i) determine or know a flowrate of the PD fluid pumped during the patient drain, (ii) determine an applied negative pressure at which the PD fluid pump is to pump the PD fluid during the patient drain, the applied pressure based on a pressure drop corresponding to the determined or known flowrate, and (iii) use sensed negative pressure from the pressure sensor to cause the PD fluid pump to pump the PD fluid during the patient drain at the applied negative pressure.

2. The PD system of claim 1, wherein the control unit is configured to repeat (i) to (iii) multiple times over the patient drain, on a time period basis or on a number of pump strokes basis.

3. The PD system of claim 1, wherein the PD fluid pump is pneumatically actuated and the pressure sensor is associated with a pneumatic line positioned and arranged to deliver negative pneumatic pressure to the PD fluid pump.

4. The PD system of claim 3, wherein the control unit is configured to accumulate known volume strokes by the PD fluid pump and/or employ an ideal gas law algorithm in determining the flowrate of the PD fluid pumped during the patient drain.

5. The PD system of claim 1, wherein the PD fluid pump is a peristaltic pump, a piston pump, or a pressure chamber pump, and wherein the pressure sensor is associated with the patient line.

6. The PD system of claim 5, wherein the control unit is configured to use an output from a flow meter associated with the patient line and/or accumulate known volume revolutions by the peristaltic pump or accumulate known volume strokes by the piston pump in determining the flowrate of the PD fluid pumped during the patient drain.

7. The PD system of claim 5, wherein the control unit is configured to use an output from a scale for the pressure chamber pump in determining the flowrate of the PD fluid pumped during the patient drain.

8. The PD system of claim 1, wherein the control unit is configured to know the flowrate, which is a commanded flowrate.

9. The PD system of claim 1, wherein the control unit is configured to determine the applied negative pressure $P_{c\ setpoint}$ by subtracting the pressure drop from an acceptable patient pressure $P_{ac}$, namely, $P_{c\ setpoint}=P_{ac}-\Delta P_{tube}(Q)$, assuming pressure drop is expressed as a positive value, wherein the acceptable patient pressure is a pressure that will not cause patient drain pain.

10. The PD system of claim 9, wherein a head height delta between the peritoneal cavity of a patient and the PD fluid pump is taken into account, such that the applied negative pressure $P_{c\ setpoint}=P_{ac}+P_{head}-\Delta P_{tube}(Q)$, wherein $P_{head}$ is determined by $\rho\times g\times\Delta h$.

11. The PD system of claim 1, wherein the control unit is configured to determine the pressure drop using an algorithm that takes into account the determined or known flowrate, at least one characteristic of the patient line, and at least one characteristic of the PD fluid.

12. The PD system of claim 11, wherein the at least one characteristic of the patient line includes a patient line length, a patient line inner diameter, and a patient line surface roughness.

13. The PD system of claim 11, wherein the at least one characteristic of the PD fluid includes PD fluid density, PD fluid viscosity, PD fluid composition and PD fluid temperature.

14. The PD system of claim 11, wherein the algorithm is dependent on whether the PD fluid flowrate is laminar or turbulent.

15. The PD system of claim 11, wherein the algorithm further takes into account a head height delta between the peritoneal cavity of a patient and the PD fluid pump.

16. The PD system of claim 1, wherein the control unit is configured to determine the pressure drop using a lookup table that correlates pressure drop and PD fluid flowrate.

17. The PD system of claim 1, wherein the control unit is configured to determine the applied negative pressure by taking into account a head height delta between the peritoneal cavity of a patient and the PD fluid pump, and wherein the control unit is configured to retake into account a head height delta between the peritoneal cavity of the patient and the PD fluid pump when (i) the pressure sensor detects a threshold unintended PD fluid pressure change or (ii) the control unit determines that a threshold unintended PD fluid flowrate has occurred.

18. The PD system of claim 17, wherein the control unit is configured to determine the head height delta between the peritoneal cavity of the patient and the PD fluid pump by slowing or stopping the PD fluid pump at least one time and reading a resulting output from the pressure sensor.

19. The PD system of claim 1, wherein the control unit is configured to use the sensed negative pressure from the pressure sensor as feedback in a pressure control routine to cause the PD fluid pump to pump the PD fluid during the patient drain at the applied negative pressure.

20. A method for minimizing patient drain pain in a peritoneal dialysis (PD) system, the method comprising:

(i) determining or knowing, by a control unit of the PD system, a flowrate of PD fluid pumped by a PD fluid pump of the PD system during a patient drain, wherein a patient line of the PD system receives used PD fluid;

(ii) determining, by the control unit, an applied negative pressure at which the PD fluid pump is to pump the PD fluid during the patient drain, the applied pressure based on a pressure drop corresponding to the determined or known flowrate; and (iii) causing, based on negative pressure associated with the PD fluid and sensed by a pressure sensor of the PD system, the PD fluid pump to pump the PD fluid during the patient drain at the applied negative pressure.

* * * * *